United States Patent [19]

Francalanci et al.

[11] Patent Number: 4,865,771
[45] Date of Patent: Sep. 12, 1989

[54] PROCESS FOR PREPARING L(−)-CARNITINE CHLORIDE FROM 3,4-EPOXYBUTYRIC ESTERS AND NOVEL INTERMEDIATE COMPOUNDS

[75] Inventors: Franco Francalanci; Marco Ricci, both of Novara; Pietro Cesti, Trecate; Carlo Venturello, Novara, all of Italy

[73] Assignee: Istituto Guido Donegani S.p.A., Novara, Italy

[21] Appl. No.: 25,351

[22] Filed: Mar. 13, 1987

[30] Foreign Application Priority Data

Mar. 14, 1986 [IT] Italy ............................. 19763 A/83

[51] Int. Cl.⁴ .................................... C07C 101/00
[52] U.S. Cl. .................................... 562/567; 435/128; 435/129; 435/135; 435/141
[58] Field of Search ................... 260/501.13; 435/128, 435/129, 135, 141

[56] References Cited

FOREIGN PATENT DOCUMENTS 2132614 7/1984 United Kingdom ............ 260/501.13

*Primary Examiner*—Paul J. Killos
*Attorney, Agent, or Firm*—Bryan, Cave, McPheeters & McRoberts

[57] ABSTRACT

A process for preparing L(−)-carnitine chloride having the formula:

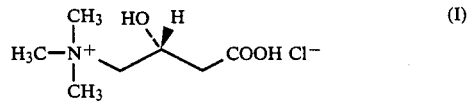

comprising the steps of:
(a) reacting a racemic ester of (R,S)-3,4-epoxybutyric acid having the formula:

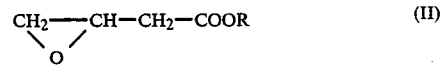

wherein R is an alkyl group having from 1-10 carbons, or a benzyl group, with an enzyme capable of selectively hydrolyzing enantiomer S(−),
(b) separating said enantiomer S(−), from non-reacted ester, which is predominantly in the R(+) form;
(c) reacting (1) the non-reacted ester obtained in step (b) with trimethylamine hydrochlorid or (2) the trimethylamine, to obtain thereby an ester having the formula:

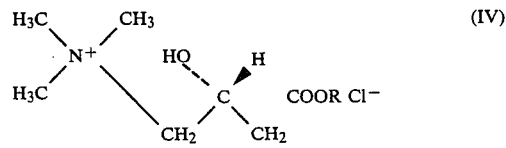

(d) hydrolyzing the ester obtain in step (c) in the presence of HCl to obtain thereby the L(−)-carnitine chloride having formula (I).

The present invention is also directed to a novel class of compounds comprising R(+) enantiomers of the esters of 3,4-epoxybutyric acid.

14 Claims, No Drawings

PROCESS FOR PREPARING L(−)-CARNITINE CHLORIDE FROM 3,4-EPOXYBUTYRIC ESTERS AND NOVEL INTERMEDIATE COMPOUNDS

TECHNICAL FIELD

The present invention relates to a process for preparing L(−)-carnitine chloride having the formula:

$$\underset{\underset{CH_3}{|}}{\overset{\overset{CH_3}{|}}{H_3C-N^+}}\diagdown\underset{HO\ H}{\diagup}\diagdown COOH\ Cl^- \qquad (I)$$

More particularly, the present invention relates to a process for preparing L(−)-carnitine chloride from esters of R(+)-3,4-epoxybutyric acid. The R(+) enantiomers of the esters are obtained by asymmetrical enzymatic hydrolysis of certain esters of the racemic 3,4-epoxybutyric acid.

The present invention is also directed to novel R(+) enantiomers of the esters of 3,4-epoxybutyric acid, which may be obtained as intermediates in the process of the invention.

It is known, that carnitine (also known as β-hydroxy-α-trimethylaminobutyric acid) has a center of asymmetry in the β position and, therefore, two stereoisomers may exist. The stereoisomers are referred to as D and L forms, antipodes, or optical enantiomers.

L(−)-carnitine chloride has an important role in human metabolism, particularly in the transfer of fatty acids. D(+)-carnitine, on the other hand, is an inhibiting agent which competes with L(−)-carnitine for the enzyme L(−)-carnitine-acyltransferase, possibly resulting in lowering the level of L(−)-carnitine present in cardiac tissue. Fritz, I. B., Schultz, S. K., J. Biol. Chem. (1965) 240 2188; Roe, C. R., Bohan, T. P., (Lancet 1982) 1411.

The commonly known therapeutic uses of L(−)-carnitine are as a eutrophyic agent and as cardioprotecting agent for the treatment of myocardial ischemias, angina pectoris, and sclerosis of the myocardium.

There are processes known for synthesizing carnitine. Most of the known processes, however, result in the production of carnitine in both the D and L forms. Thus, an additional step is required for separating the racemic mixture into its two single optical enantiomers. These known processes require expensive reactants which are optically active, such as, for example, dibenzoyltartaric acid, camphoric acid, mandelic acid and the like. Additionally, the reaction conditions must be carefully controlled. Also, several crystallization steps are necessary. Consequently, known processes for synthesizing L(−)-carnitine are generally economically burdensome and thus impractical for industrial application. (See European Patent Application EP No. 141,408; French Pat. No. 1,466,696 and British Pat. No. GB.-A-2,131,049).

There is also described a process for synthesizing L(−)-carnitine from an optically active compound such as D-mannitol (see European Patent Application EP No. 60,595). While this process does not require any separation of D and L enantiomers, the synthesis is complex in that a large number of individual steps must be performed. Moreover, expensive and potentially dangerous reactants such as lead tetraacetate are used in the process.

Some microbiological processes for preparing L(−)-carnitine from prochiralic substrates, such as alkyl chloroacetoacetates, crotonobetaines, or butyrobetaines are also known (see Belgian Pat. BE No. 898,396, European Patent Application EP No. 122,794; French Patent Application FR No. 2,485,564). Such processes have the disadvantages of requiring bulky reaction volumes, and resulting in low yields and difficulty in purifying the products.

Therefore there is a need for a simple, efficient and economical process for preparing L(−)-carnitine on an industrial scale.

The present invention provides a method for the preparation of L(−)-carnitine chloride which is simple to perform and advantageous from an industrial standpoint.

The present invention also provides a new class of intermediate compounds of the R(+) forms of certain esters of 3,4-epoxybutyric acid.

SUMMARY OF THE INVENTION

It has now been found that L(−)-carnitine chloride may be prepared by a process comprising asymmetrically hydrolyzing racemic esters of 3,4-epoxybutyric acid to resolve the R(+) enantiomer, reacting the R(+) enantiomer with trimethylamine hydrochloride or its corresponding chlorohydrin with trimethylamine, followed by acid hydrolysis to obtain thereby the desired L(−)-carnitine chloride.

The enzymatic hydrolysis is effected by specific enzymes or microorganisms capable of producing the enzymes, said enzymes being capable of selectively hydrolyzing the enantiomer S(−) of the racemic ester 3,4-epoxybutyric acid.

In accordance with another embodiment of the invention, there is provided a new class of compounds which comprises the R(+) enantiomers of the racemic esters of 3,4-epoxybutyric acid. The R(+) enantiomers may be obtained by the enzymatic asymmetric hydrolysis of the racemic esters.

DETAILED DESCRIPTION OF THE INVENTION

The present invention provides a process for preparing L(−)-carnitine chloride, having the formula $$\underset{\underset{CH_3}{|}}{\overset{\overset{CH_3}{|}}{H_3C-N^+}}\diagdown\underset{HO\ H}{\diagup}\diagdown COOH\ Cl^- \qquad (I)$$

comprising the steps of:

(a) reacting a racemic ester of (R,S)-3,4-epoxybutyric acid having the formula:

$$CH_2\underset{O}{\overset{}{\diagdown\diagup}}CH-CH_2-COOR \qquad (II)$$

wherein R is an alkyl group having from 1-10 carbons or a benzyl group, with an enzyme capable of selectively hydrolyzing enantiomer S(−), asymmetrically, the reaction being carried out under controlled pH conditions;

(b) separating the hydrolyzed enantiomer S(−) from non-reacted ester (II), present as predominantly the R(+) enantiomer;

(c) reacting the nonreacted ester obtained in step (b), with trimethylamine hydrochloride to obtain thereby an ester having the formula

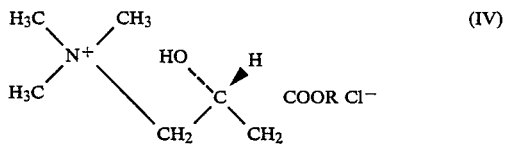

wherein R is an alkyl group having from 1-10 carbons or a benzyl group; and (d) hydrolyzing the ester obtained in step (c) in the presence of HCl, to obtain thereby L(—)-carnitine chloride having formula (I).

In another embodiment of the process of the invention, hydrolysis of the racemic ester of (R,S)-3,4-epoxybutyric acid may be carried out in the presence of a microorganism capable of producing an enzyme for selectively hydrolyzing, asymmetrically, the enantiomer S(—).

In yet another embodiment of the process of the invention, the non-reacted R(+) enantiomer obtained in step (b) may be converted into its corresponding chlorohydrin having the formula

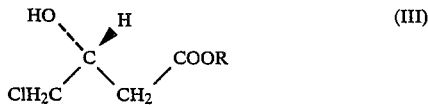

prior to reacting with trimethylamine. The conversion of the R(+) enantiomer into the chlorohydrin may be carried out by known techniques.

The present invention also provides a new class of intermediate compounds comprising the R(+) enantiomers of the racemic esters of formula (II).

Resolution of the racemic esters of formula (II) into the respective enantiomers is not easily effected by known methods. On the contrary, in accordance with the present invention, the racemic esters are simply resolved.

The resolution process is represented schematically as follows:

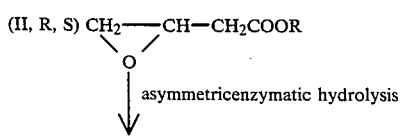

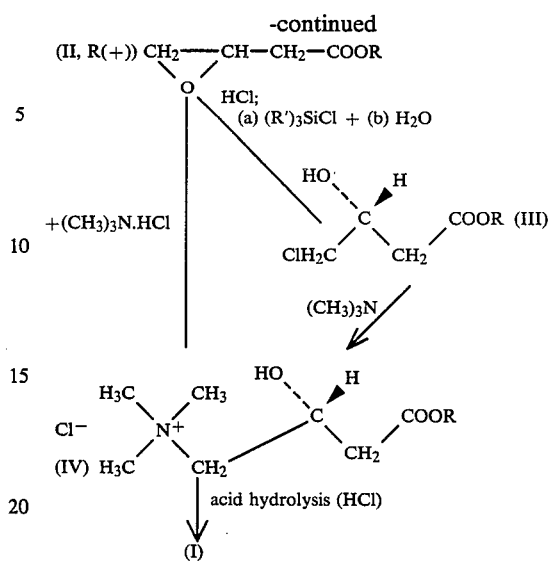

wherein R is an alkyl group having from 1-10 carbons or a benzyl group, and R' is an alkyl group having from 1-5 carbons.

The racemic esters of formula (II) are known compounds and may be prepared according to known methods, for example:

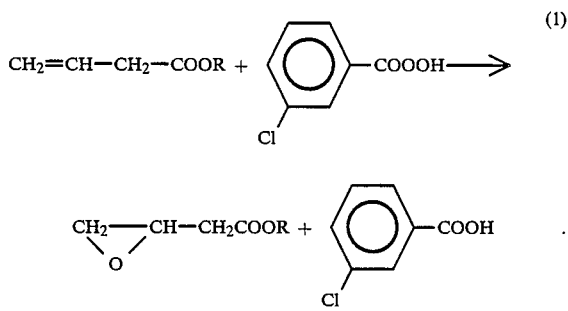

[(Pharm. Sci.) 64, 1262 (1975)]

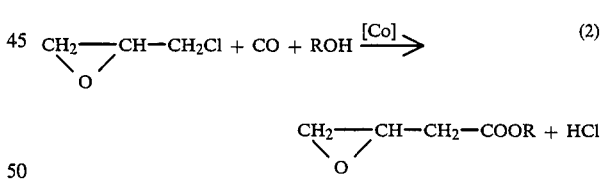

As previously discussed, the racemic esters of formula (II) are reacted with enzymes capable of selectively hydrolyzing only the enantiomer S(—). Useful enzyme may be obtained from microorganisms or may be of animal origin, provided that the enzyme is capable of selectively hydrolyzing enantiomer S(—), leaving the enantiomer R(+) substantially unaltered (asymmetric hydrolysis).

Known enzymes have been found to be useful for this purpose. Examples of suitable enzymes which have been found to be particularly effective are:

| ENZYME | ORIGIN | PRODUCER |
|---|---|---|
| Steapsin | swine pancreas | SIGMA Chem. Co. St. Louis - USA |
| Pancreatin | swine pancreas | UNIBOS - Trecate (Italy) |

| -continued | | |
|---|---|---|
| ENZYME | ORIGIN | PRODUCER |
| Lipase from *Candida cylindracea* | *Candida cylindracea* | SIGMA Chem. Co. St Louis - USA |
| Esterase from swine liver | swine liver | SIGMA Chem. Co. St Louis - USA |

It should be understood, however, that other enzymes capable of the required selective hydrolysis as are known to those skilled in the art are also useful.

As previously discussed, the hydrolysis of the racemic esters may also be carried out in the presence of microorganisms producing appropriate hydrolytic enzymes.

Thus, any microorganism, which produces enzymes capable of hydrolyzing, asymmetrically, the racemic esters having formula (II) are useful.

The following microorganisms have been found to be particularly effective:

| | | |
|---|---|---|
| *Pseudomonas fragi* | IFO | 3458 |
| *Bacillus subtilis* | ATCC | 6633 |
| *Rodotorula minuta* | IFO | 0879 |
| *Candida cylindracea* | ATCC | 14830 |
| *Arthrobacter simplex* | IFO | 3530 |

In carrying out the method of the invention, the asymmetric hydrolysis of the racemic esters of formula (II) [step (a)] is carried out with vigorous stirring of a mixture comprising the racemic ester and enzyme. Typically, the enzyme is present in an amount ranging from between 0.03–10% by weight of the racemic ester. The concentration of the racemic ester is generally from between 1–20% by weight of the reaction mixture. In a preferred embodiment, an aqueous solution of a raw or purified enzyme is added. Alternatively, the enzyme may be immobilized on suitable substrates as are known to those skilled in the art.

In another embodiment of the present invention, the racemic ester is mixed with a broth containing a microorganism capable of elaborating the required enzyme, or a filtrate, concentrate or suspension of the microorganism, as the source of the hydrolyzing enzyme.

The hydrolysis of step (a) is carried out at a temperature from between about 5° C. to 60° C., preferably from between 10° C. to 30° C.

The pH of the reaction mixture is maintained from between about 5 and 9, preferably from between 6 and 8. It is believed that the enzymes are most active in a pH range of from about 5 to 9. The pH of the reaction mixture is controlled with a buffer, preferably a sodium and/or potassium buffer solution. Another method of controlling the pH of the reaction mixture is by neutralizing the acids formed during the reaction with a mineral base such as, for example, NaOH, KOH, LiOH, $CaCO_3$, and the like.

Typically, the asymmetric hydrolysis of the racemic ester [step (a)] proceeds for a period of from about 5 to 72 hours, depending on the specific activity of the enzyme used or the amount of conversion desired.

When the reaction of asymmetric hydrolysis is complete, the non-reacted ester formula (II), rich in enantiomer R(+), is separated from the reaction mixture by using a solvent immiscible with water. Known separation techniques are useful for this purpose. Suitable solvents useful in the separation include methylene chloride, toluene, ligroine, ethyl ether etc. The extracted R(+) enantiomer is then purified according to known techniques such as, for example, distillation or column chromatography.

Epoxyester (II), which is predominantly the R(+) enantiomer, resulting from the asymmetric hydrolysis is then reacted with trimethylamine hydrochloride to obtain an ester of formula (IV). In practice, the reaction is performed by stirring a solution comprising the epoxyester (II), trimethylamine hydrochloride and a $C_1$-$C_4$ aliphatic (hydro)-alcoholic solvent. The reaction is carried out at a temperature from between about 10° C. to 80° C., preferably from between about 20° C. to 60° C. The reaction time typically is from between about 1 to 120 hours, depending on the temperature of the reaction mixture. The concentration of epoxyester R(+) (II) in the reaction mixture is from between about 10% to 60%. The amount of trimethylamine hydrochloride used, is from between about 0.3 and 1 mole per mole of epoxyester R(+) (II), preferably about 0.5 mole per mole. When the reaction is completed, the (hydro)-alcoholic solvent is distilled off leaving a residue which is treated with water and washed with a solvent immiscible with water. Suitable solvents include methylene chloride, ethyl ester etc. Then, the water is distilled off to obtain thereby an ester having formula (IV).

The ester is converted into L(−)-carnitine chloride by acid hydrolysis with aqueous hydrochloric acid. The acid hydrolysis is carried out at a temperature from between about 15° C. to 100° C., preferably from between about 80° C. to 100° C. The reaction times are from between about 1 to 20 hours, depending upon the temperature used. Hydrochloric acid concentrated from between 5% and 37% is used in an amount from about 1 to 10 moles per mole of the ester of formula (IV).

When the hydrolysis reaction is completed, the solution obtained is evaporated at a reduced pressure, leaving a residue which is crystallized, in accordance with known techniques, to obtain thereby the L(−)-carnitine chloride of formula (I).

In accordance with one embodiment of the present invention, the ester of formula (IV) may be obtained as follows. Epoxyester (II) predominantly as enantiomer R(+), which is recovered from the enzymatic asymmetric hydrolysis, is converted into its corresponding chlorohydrin formula (III), by reacting with aqueous hydrochloric acid. The conversion reaction is effected by dropwise addition of concentrated aqueous hydrochloric acid into a solution of the epoxyester, enantiomer R(+) in tetrahyrofuran, or an ether solvent immiscible with water. The temperature of the conversion reaction is from between about 0° C. to 30° C., preferably from between about 0° C. to 10° C. The reaction time generally is from between about 1 to 4 hours, depending upon the reaction conditions. Typically, the amount of hydrochloric acid necessary to effect the conversion is from between about 1 to 2 moles per mole of epoxyester R(+) (II), preferably from between about 1.0 to 1.1 moles per mole. When the desired conversion is achieved, the reaction mixture is neutralized with a base, preferably $Na_2CO_3$, although other bases as are known to those skilled in the art are also useful. The reaction mixture is then saturated with $Na_2SO_4$, NaCl or $Na_2CO_3$, and extracted with a solvent immiscible with water. Suitable solvents include methylene chloride or ethyl ether. The solvent is then distilled off leaving a raw chlorohydrin of formula (III).

The chlorohydrin is subsequently converted into the ester of formula (IV) by reaction with trimethylamine in an aqueous alcoholic or alcoholic solvent. Suitable solvents include water, and $C_1-C_4$ alcohols such as ethanol and methanol, and water-alcohol mixtures.

In practice, the reaction is carried out by adding a trimethylamine solution to the chlorohydrin (III) and stirring the resulting mixture at a temperature from between about 20° C. to 100° C., preferably from between about 80° C. and 90° C., for from between about 1 to 20 hours. The reaction time varies depending upon the temperature of the reaction mixture. The concentration of the trimethylamine solution is from between about 5% to 33%, and preferably from between about 25% to 33%. The amine content is from between about 1 to 10 moles per mole of chlorohydrin (III), and preferably from between about 2 to 3 moles per mole. When the reaction is completed, any excess trimethylamine and solvent are distilled off to obtain a raw ester of formula (IV). The raw ester is hydrolyzed, as previously described, to obtain the desired L(−)-carnitine.

The chlorohydrin of formula (III), may also be obtained by reacting the epoxyester, R(+) enantiomer, with a chlorinated silane compound having formula $(R')_3$ SiCl, wherein R' is an alkyl having from 1-5 carbons. In accordance with one embodiment of the present invention, the epoxyester, predominantly as the R(+) enantiomer, resulting from the enzymatic asymmetric hydrolysis of (R,S)-3,4-epoxybutyric acid is converted to its corresponding chlorohydrin by reacting the epoxyester with a chloro-($C_1-C_5$) trialkylsilane, preferably, chlorotrimethylsilane, followed by hydrolysis with water.

In practice, the enantiomer R(+) of an ester of formula II is dissolved in an excess of a chlorosilanic compound. The mixture is allowed to react for at least one day at room temperature.

When the reaction is completed, the excess silane is evaporated, leaving a residue, which is treated with hydroalcoholic (ethanol) HCl and dried again, thereby obtaining a raw chlorohydrin having formula (III). The chlorohydrin thus obtained may be acid hydrolyzed, as previously described, to obtain thereby L(−)-carnitine of formula I.

The L(−)-carnitine chloride prepared in accordance with the present invention may be used to obtain other derivatives of L(−)-carnitine, such as inorganic salts (HBr, etc.) or organic acids (oxalic acid, etc.).

The following examples are illustrative of the present invention and should not be construed as a limitation thereof.

The following abbreviations are used:

Eu (hfc)$_3$—europium tris [3-(heptafluoropropylhydroxymethylene)-d-camphorate].

e.e. = enantiomeric excess.

a.s. = as such.

The e.e. of R(+)-3,4-epoxybutyrates having formula (II) was determined by N.M.R. analysis at 300 MHz, in the presence of Eu(hfc)$_3$ (0.05 moles per mole of ester).

EXAMPLE 1

Step (a)

To 45 ml of a 0.1M KCl solution, the following ingredients were added:

(1) 45 ml of a buffer solution consisting of Na phosphate at pH=7;

(2) 10 g of isobutyl (R,S)-3,4-epoxybutyrate (63.3 mmoles); and (3) 640 mg of steapsin enzyme (swine pancreas lipase available from SIGMA Chem. Co., USA having a protein content of 35% and an activity equal to 35-70 units per mg of protein). The reaction mixture was vigorously stirred for 22 hours at 20° C. During the reaction time, the pH was kept constant at 7 by adding an aqueous solution of 5N NaOH. At the end of the 22 hour reaction period (65% conversion of 3,4-epoxybutyrate), the unreacted ester was recovered from the reaction mixture by extraction with methylene chloride purified by distillation.

3.3 g of isobutyl R(+)-3,4-epoxybutyrate was recovered: $[\alpha]_D^{20} = +9.90°$ (a.s.); $^1$H-NMR (CDCL$_3$): 50.94 (d, 6H), 1.87–2.03 (m, 1H), 2.50–2.66 (m, 3H), 2.82–2.88 (m, 1H), 3.27–3.34 (m, 1H), 3.92 (d, 2H).

NMR analysis at 300 MHz, in the presence of Eu(hfc)$_3$ (0.05 moles per mole of ester) showed an e.e. ≧ 90%.

Steps (b)+(c)

3.3 g of isobutyl R(+)-3,4-epoxybutyrate (20.9 mmoles) was dissolved in 4 ml of methanol, and then, 1 g of trimethylamine hydrochloride (10.46 mmoles) was added. The resulting solution was brought to 45° and vigorously stirred for 2 hours. The methanol was then distilled off leaving a residue which was treated with water and ether, resulting in aqueous and organic phases. The phases were separated, using known techniques. The organic phase was washed with water, and added to the aqueous phase, followed by washing with ether. The resulting solution was concentrated, and then, 3 ml of concentrated aqueous hydrochloric acid was added. The solution was reflux heated for two hours and then evaporated at reduced pressure (about 20 mmHg). Any remaining water was removed by azeotropic distillation with ter-butyl alcohol. A yield of 1.19 g of L(−)-carnitine chloride was obtained,: $[\alpha]_D^{20} = -21.2°$ C. (c=1, H$_2$O); e.e. ≧ 90%.

EXAMPLE 2

Step (a)

The reaction mixture was prepared as in Example I, step (a), except using 10 g of n-butyl (R,S)-3,4-epoxybutyrate (63.3 mmoles). After 26 hours (60% ester conversion), 3.8 g n-butyl R(+)-3,4-epoxybutyrate were recovered by extraction with methylene chloride and subsequent distillation: $[\alpha]_D^{20} = 8.10°$ (a.s.); $^1$H-NMR (CDCl$_3$): 0.94 (t. 3H), 1.32–1.47 (m, 2H), 1.58–1.70 (m, 2H), 2.53–2.60 (m, 3H), 2.82–2.88 (m, 1H), 3.27–3.35 (m, 1H), 4.13 (t. 2H).

NMR analysis at 300 MHz, in the presence of Eu (hfc)$_3$, showed an e.e. ≧ 90%.

Steps (b)+(c)

The reaction mixture was prepared as in Example 1, steps (b) and (c) except using the 3.8 g of n-butyl R(+)-3,4-epoxybutyrate (24.05 mmoles obtained in step (a) hereof, and 1.15 g of trimethylamine hydrochloride (12.0 mmoles). A yield of 1.75 g of L(−)-carnitine chloride were obtained: $[\alpha]_D^{20} = -21.3°$ (c=1, H$_2$O); e.e. ≧ 90%.

EXAMPLES 3–8

The processes were performed as in Example 1, except for the changes indicated on Table 1. The yields are also reported in Table 1.

EXAMPLE 9

Step (a)

50 ml of nutrient broth (available from Oxoid Ltd., UK) in 250 ml flash was inoculated with the content of a slant of *Arthrobacter Simplex* (IFO 3530) and incubated for 18 hours at 37° C. with stirring at 200 revolutions per minute.

Then, 100 ml of nutrient broth in a 500 ml flask were inoculated with 4 ml of the grown culture and incubated for 12 hours at 37° C. with stirring at 200 revolutions per minute.

Then, 50 ml of a potassium phosphate buffer solution at pH-7, and 5 g of isobutyl (R,S)-3,4-epoxybutyrate were added to the flask containing the culture, and the resulting reaction mixture was stirred for 48 hours at 20° C.

At the end of the reaction period, the mixture was extracted with methylene chloride, the solvent was evaporated leaving a residue containing isobutyl 3,4-epoxybutyrate. The residue was purified by chromatography on a silica column. 2.25 g of isobutyl R(+)-3,4-epoxybutyrate having an e.e.=75% was recovered.

Steps (b)+(c)

The process set forth in steps (b) and (c) of Example 1 were followed. A yield of 0.84 g of L(−)-carnitine chloride having an e.e.=75% was obtained.

EXAMPLE 10

The procedure of Example 9 was followed with the microorganism *Pseudomonas fragi* (IFO 3458). 2.35 g of isobutyl R(+)-3,4-epoxybutyrate having an e.e.=56% was obtained from step (a). From this ester, a yield of 0.82 g of L(−)-carnitine chloride having an e.e.=55% was obtained.

EXAMPLE 11

The procedure of Example 9 was followed with the microorganism [Bacillus subtilis (ATCC 6633). 2.85 g of isobutyl R(+)-3,4-epoxybutyrate having an e.e.=52% was obtained from step (a). From this ester, a yield of 1.0 g of L(−)-carnitine chloride having an e.e.=52% was obtained.

EXAMPLE 12

Step (a)

50 ml of a culture medium having the following composition:
0.3% of yeast extract (from Oxoid Ltd. UK),
1% of peptone (from Oxoid Ltd. UK), and
2% of glucose was inoculated with the content of a slant of *Rodotorula minuta* (IFO 0879).

The inoculated medium was placed into a 500 ml flask and incubated for 18 hours at 28° C. with stirring at 160 revolutions per minute.

4 ml of the grown culture were drawn and used to inoculate 100 ml of a culture medium having the composition previously described.

0.5 g of calcium carbonate were added and the resulting reaction mixture was maintained at 28° C. with stirring at 160 revolutions per minute.

After 24 hours, 5 g of isobutyl (R,S)-3,4-epoxybutyrate were added to the reaction mixture and maintained at 20° C. for 72 hours, with stirring.

At the end of the reaction time, the mixture was extracted with the solvent methylene chloride. The solvent was evaporated, leaving a residue containing isobutyl R(+)-3,4-epoxybutyrate acid which was purified by chromatography on a silica column.

3.1 of isobutyl R(+)-3,4-epoxybutyrate having an e.e.=27% was obtained.

Steps (b)+(c)

The procedure set forth in steps (b) and (c) of Example 1 was followed. A yield of 1.16 g of L(−)-carnitine chloride having an e.e.=27% was obtained.

EXAMPLE 13

The procedure of Example 12 was followed with the microorganism *Candida cylindracea* (ATCC 14830). 2.75 g of isobutyl R(+)-3,4-epoxybutyrate having an e.e.=47% was obtained from step (a). From this ester a yield of 0.93 g of L(−)-carnitine chloride having an e.e.=45% was obtained.

EXAMPLE 14

Step (a)

The procedure of Example, step (a) was followed and 3.2 g of isobutyl R(+)-3,4-epoxybutyrate having an e.e.=90% were obtained.

Steps (b)+(c)

The 3.2 g of isobutyl R(+)-3,4-epoxybutyrate obtained in step (a) was dissolved in 40 ml of tetrahydrofuran. Into the resulting solution, 1.66 ml of concentrated aqueous hydrochloric acid was added, dropwise, for about one hour. The solution was cooled to a temperature from between about 0° to 5° C., in an ice bath and vigorously stirred. Then the temperature of the resulting solution was permitted to rise to 20° C. with continued stirring one hour. The solution was then saturated with $Na_2CO_3$, concentrated and extracted with ether. The ether extract was dried on $Na_2SO_4$, filtered and evaporated under reduced pressure, thereby obtaining 3.26 g of an oil of isobutyl R(+)-4-chloro-3-hydroxybutyrate (III) which when analyzed was shown to have a gas chromatographic titre of 94%. The oil was dissolved in 8 ml of ethanol and 8 ml of an aqueous solution of 5.19M trimethylamine. The resulting solution was reflux heated, with vigorous stirring, for two hours. After 2 hours, the solution was evaporated, under reduced pressure leaving a residue which was treated with 30 ml of aqueous concentrated hydrochloric acid followed by reflux heating for two hours, with stirring. After 2 hours, the solution was evaporated under reduced pressure, and subjected to azeotropic distillation with ter-butyl alcohol to remove any remaining traces of water. A yield of 1.13 g of L(−)-carnitine chloride were obtained: $[\alpha]_D^{20} = -15.4°$; e.e.=65%.

EXAMPLE 15

The procedure of Example 1, step (a) was followed and 3.2 g of isobutyl R(+)-3,4-epoxybutyrate having an e.e.=90% were obtained.

Steps (b)+(c)

The 3.2 g of isobutyl R(+)-3,4-epoxybutyrate obtained in step (a) was dissolved in 12 ml of chlorotrimethylsilane and the resulting solution was stirred at room temperature for 20 hours. The excess chloromethylsilane was removed by distillation, leaving a residue which was treated with 30 ml of methanol and 1 ml of 10% aqueous hydrochloric acid. The resulting solution was stirred, at room temperature, for 10 minutes. Then, the solution was evaporated at reduced pressure leaving a residue which was treated with ether and washed with water, resulting in organic and aqueous phases. The organic (ether) phase was dried on $Na_2SO_4$, filtered and evaporated. 3.84 g of isobutyl R(+)-4-chloro-3-hydroxybutyrate (III), having a gas chromatographic titre of 90% was obtained. The procedure of steps (b) and (c) of Example 14 were followed, and a yield of 1.20 g of L(−)-carnitine chloride, $[\alpha]_D^{20} = -14.3°$; e.e.=60% was obtained.

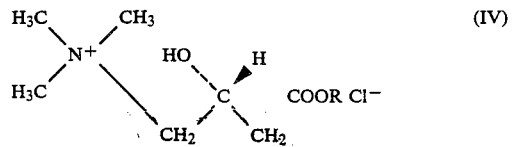

TABLE I

| Example No. | R | Step (A) ENZYME (Amount) | TIME (hours) | ESTER CONV. % | CHARACTERISTICS R(+)-3,4 quoxybutyrate NMR, δ | $[\alpha]_D^{20}$ | e.e | g. of CARNITINE CHLORIDE | e.e. CARNITINE CHLORIDE |
|---|---|---|---|---|---|---|---|---|---|
| 3 | iso-butyl | Lipase from *Candida Cylindracea* (400 mg) | 39 | 57% | 0,94 (6H); 1,87–2,03 m (1H) 2,50–2,66 m (3H); 2,82–2,88 m (1H); 3,27–3,34 m (1H); 3,92 d (2H) | | | | |
| 4 | iso-butyl | Esterase from swine liver (3.5 mg) | 58 | 52% | " | +6.82 | 62% | 1.60 | 61% |
| 5 | iso-butyl | Pancreatin (240 mg) | 21 | 60% | " | +8.25 | 75% | 1.30 | 74% |
| 6 | n-octyl | Steapsin (500 mg) | 24 | 60% | t (3H); 1,16–1,42 m (10H); 1,58–1,71 m (2H); 2,53–2,61 m (3H); 2,82–2,88 m (1H); 3,25–3,33 m (1H); 4,12 t (2H) | +4,73 | ≧95% | 1.60 | 95% |
| 7 | methyl | Lipase from *Candida Cylindracea* (400 mg) | 48 | 60% | 2,54–2,60 m (3H); 2,83–2,88 m (1H); 3,26–3,34 m (1H); 3,74 s (3H) | n.d. | 50% | 1.41 | 50% |
| 8 | benzyl | Steapsin (500 mg) | 6.5 | 62% | 2,55–2,57 m (1H); 2,61–2,63 m (2H); 2,82–2,85 m (1H); 3,27–2,35 m (1H); 5,17 s (2H); 7,25–7,37 m (5H) | n.d. | 58% | 1.67 | 60% |

We claim:

1. A process for preparing L(−)-carnitine chloride having the formula:

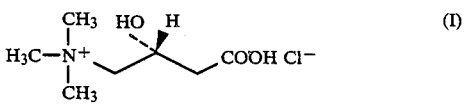

comprising the steps of:
(a) reacting a racemic ester of (R,S)-3,4-epoxybutyric acid having the formula:

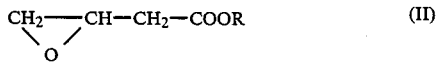

wherein R is an alkyl group having 1–10 carbons or a benzyl group, with an enzyme or a microorganism producing said enzyme, the enzyme capable of selectively hydrolyzing enantiomer S(−), the reaction being carried out under controlled pH conditions;
(b) separating the enantiomer S(−) from non-reacted ester, present predominantly as the R(+) enantiomer;
(c) reacting (1) the non-reacted ester obtained in step (b) with trimethylamine hydrochloride or (2) the chlorohydrin derivative of said ester with trimethylamine, to obtain thereby an ester having the formula:

wherein R is an alkyl group having 1–10 carbons or a benzyl group; and
(d) hydrolyzing the ester obtained in step (c) in the presence of HCl to obtain thereby the L(−)-carnitine chloride having formula (I).

2. The process of claim 1, wherein the selective hydrolysis of enantiomer S(−) is effected with an enzyme selected from the group consisting of steapsin, pancreatin, lipase obtainable from *Candida Cylindracea*, and esterase obtainable from swine liver.

3. The process of claim 1, wherein the selective hydrolysis of enantiomer S(−) is effected with an enzyme produced by a microorganism, selected from the group consisting of *Pseudomonas fragi* (IFO 3458), *Bacillus subtilis* (ATCC 6633), *Rodotorula minuta* (IFO 0879), *Candida cylindracea* (ATCC 14830), and *Arthrobacter simplex* (IFO 3530).

4. The process of claim 3, wherein the microbial enzyme is obtainable from a microbial culture broth, filtrate, concentrate or suspension of cells.

5. The process of claim 2, wherein the enzyme is immobilized on a substrate.

6. The process of claim 1, wherein in step (a) the asymmetrical hydrolysis of the racemic ester is effected with the enzyme present in from about 0.03% to 10% by weight of the racemic ester.

7. The process of claim 1, wherein in step (a) the asymmetrical hydrolysis of the racemic ester is carried out at a temperature of from between about 10° C. to 30° C.

8. The process of claim 1, wherein in step (a) the asymmetrical hydrolysis of the racemic ester is carried out at a pH value of from between 5 to 9.

9. The process of claim 1, wherein in step (a) the concentration of the racemic ester is from about 1% to 20% by weight of the reaction mixture.

10. The process of claim 1, wherein in step (c) the non-reacted ester is converted into the ester of formula (IV) by reaction with trimethylamine hydrochloride in a $C_1$-$C_4$ aliphatic (hydro)-alcoholic solvent, at a temperature from about 10° C. and 80° C., in a molar ratio of $(CH_3)_3$ N.HCl: non-reacted ester enantiomer from about 0.3:1 to 1:1.

11. The process of claim 1, wherein in step (c) the conversion of the non-reacted ester into the ester of formula IV is effected by reacting said non-reacted ester with aqueous HCl, wherein the HCl is in at least equimolar ratio with the water, in the presencee of an ether solvent, immiscible with water, at from about 0°-30° C. to obtain thereby the chlorohydrin derivative of the non-reacted ester, and treating said chlorohydrin derivative with an at least equimolar trimethylamine in a ($C_1$-$C_4$) hydro-alcoholic or aqueous medium at from about 20°-100° C., to obtain thereby the ester of formula IV.

12. The process of claim 11, wherein the non-reacted ester is converted chlorohydrin derivative by reaction with a chloro-alkylsilane compound having the formula $(R')_3$ SiCl, wherein R' is an alkyl group having 1-5 carbons.

13. The process of claim 1, wherein the acid hydrolysis of the ester obtained in step (c) is carried out with aqueous HCl at a temperature ranging from about 15° C. to 100° C., wherein the HCl is at an equimolar ratio with the water.

14. The process of claim 1, wherein in step (c) the conversion of the non-reacted ester into the ester of formula IV is effected by reacting said non-reacted ester with aqueous HCl, wherein the HCl is in at least equimolar ratio with the water, in the presence of tetrahydrofuran at from about 0°-30° C., to obtain thereby the chlorohydrin derivative of the non-reacted ester, and treating said chlorohydrin derivative with an at least equimolar trimethylamine in a ($C_1$-$C_4$) hydro-alcoholic or aqueous medium at from about 20°-100° C., to obtain thereby the ester of formula IV.

* * * * *